United States Patent
Kabilan et al.

(10) Patent No.: US 8,334,140 B2
(45) Date of Patent: Dec. 18, 2012

(54) BORONATE COMPLEX AND ITS USE IN A GLUCOSE SENSOR

(75) Inventors: Satyamoorthy Kabilan, Cambridge (GB); Mei-Ching Lee, Middlesex (GB); Adrian Martin Horgan, Cambridge (GB); Kathryn Elizabeth Sorrell Medlock, Cambridge (GB); Christopher Robin Lowe, Cambridge (GB); Jeffrey Blyth, Cambridge (GB)

(73) Assignees: Smart Holograms Limited, Cambridge (GB); Cambridge Enterprise Limited, Cambridge (GB)

( * ) Notice: Subject to any disclaimer, the term of this patent is extended or adjusted under 35 U.S.C. 154(b) by 704 days.

(21) Appl. No.: 12/093,038

(22) PCT Filed: Nov. 8, 2006

(86) PCT No.: PCT/GB2006/004172
§ 371 (c)(1),
(2), (4) Date: Oct. 9, 2009

(87) PCT Pub. No.: WO2007/054689
PCT Pub. Date: May 18, 2007

(65) Prior Publication Data
US 2010/0167416 A1    Jul. 1, 2010

Related U.S. Application Data

(60) Provisional application No. 60/843,358, filed on Sep. 7, 2006.

(30) Foreign Application Priority Data

Nov. 8, 2005 (GB) .................................. 0522796.2

(51) Int. Cl.
*G01N 33/00* (2006.01)
(52) U.S. Cl. ........ 436/95; 422/68.1; 435/14; 435/287.1; 435/288.7
(58) Field of Classification Search .................... None
See application file for complete search history.

(56) References Cited

U.S. PATENT DOCUMENTS

| 5,342,672 | A | 8/1994 | Killey |
| 6,682,938 | B1 | 1/2004 | Satcher, Jr. et al. |
| 7,998,412 | B2 * | 8/2011 | Burles et al. ............... 422/82.05 |
| 8,048,680 | B2 * | 11/2011 | Lowe et al. .................... 436/95 |
| 2002/0128234 | A1 * | 9/2002 | Hubbell et al. ............... 514/100 |
| 2004/0028612 | A1 * | 2/2004 | Singaram et al. ............. 424/9.6 |

(Continued)

FOREIGN PATENT DOCUMENTS
JP    04-124144    4/1992

(Continued)

OTHER PUBLICATIONS

Horgan et al., Crosslinking of phenylboronic acid receptors as a means of glucose selective holographic detection, Jan. 2006, Biosensors and Bioelectronics 21: pp. 1838-1845.*

(Continued)

*Primary Examiner* — Nelson Yang
(74) *Attorney, Agent, or Firm* — Saliwanchik, Lloyd & Eisenschenk

(57) ABSTRACT

A sensor comprises respective acceptor and donor compounds immobilised in or on a matrix including a glucose-binding boronate and a cationic species, whereby the spacing between the acceptor and donor compounds is reduced in the presence of glucose. For example a holographic sensor comprises a glucose-binding boronate and a cationic species held within the sensor.

26 Claims, 7 Drawing Sheets

U.S. PATENT DOCUMENTS

2008/0020478 A1* 1/2008 Lowe et al. .................. 436/127
2011/0286064 A1* 11/2011 Burles et al. .................... 359/19

FOREIGN PATENT DOCUMENTS

| WO | WO 01/50113 | 7/2001 |
|---|---|---|
| WO | WO 03/087899 | 10/2003 |
| WO | WO 2004/081624 | 9/2004 |
| WO | WO 2005/015184 | 2/2005 |
| WO | WO 2005/031442 | 4/2005 |
| WO | WO 2005/121753 | 12/2005 |
| WO | WO 2005/122099 | 12/2005 |

OTHER PUBLICATIONS

Wang et al., Glucose-responsive vesicular sensor based on boronic acid-glucose recognition in the ARS/PBA/DBBTAB covesicles, Feb. 2006, Sensors and Actuators B 119: pp. 695-700.*

Kabilan et al., Glucose-sensitive holographic sensors, 2004, J Molec Recog, 17: pp. 162-166.*

Badugu, R. et al., "Fluorescence sensors for monosaccharides based on the 6-methylquinolinium nucleus and boronic acid moiety: potential application to ophthalmic diagnostics," *Talants*, Feb. 2005, vol. 65, No. 3, pp. 762-768.

Horgan, A.M. et al., "Crosslinking of phenylboronic acid receptors as a means of glucose selective holographic detection," *Biosensors and Bioelectronics*, Mar. 2006, vol. 21, No. 9, pp. 1838-1845.

Matsumoto, M. et al., "Separation of sugar by solvent extraction with phenylboronic acid and trioctylmethylammonium chloride," *Separation and Purification Technology*, Jun. 2005, vol. 43, No. 3, pp. 269-274.

* cited by examiner

BORONATE COMPLEX AND ITS USE IN A GLUCOSE SENSOR

This application is a National Stage Application of International Application Number PCT/GB2006/004172, filed Nov. 8, 2006, which claims priority to Great Britain Application No. 0522796.2, filed Nov. 8, 2005 and claims the benefit of U.S. Application No. 60/843,358, filed Sep. 7, 2006, which are incorporated herein in their entirety.

FIELD OF THE INVENTION

This invention relates to a novel boronate complex and its use in a glucose sensor.

BACKGROUND OF THE INVENTION

Reliable personal glucose monitoring devices are of critical importance to diabetics. Currently, determination of blood glucose is achieved using hand-held devices, which require invasive pin-prick sampling of blood glucose levels. These tests are painful, inconvenient, need to be performed several times per day, do not provide a continuous measurement and risk missing important fluctuations in glucose levels.

Subcutaneous, implantable sensors that remain in permanent contact with interstitial fluid, or contact lens sensors that measure glucose levels in tear fluid, may be used to perform non-invasive blood glucose monitoring. Enzyme-based systems that are currently used for invasive blood glucose monitoring using glucose oxidase, are unlikely to be suitable for this purpose. Their relatively high cost, inadequate stability and lack of sterilisability complicate their use in vivo. Therefore, glucose-responsive devices are required that mimic the selectivity and specificity of enzyme-based systems, whilst offering a more robust and sterilisable detection system.

Boronic acids are weak Lewis acids; the electron-deficient boron atom exists in either an uncharged planar trigonal form or, when interacting with a strong base such as hydroxide, a charged tetrahedral form. Both forms may covalently bind vicinal diols with the reversible formation of a boronic acid diester and the liberation of two equivalents of water. The $pK_a$ of the boronic acid diester is significantly reduced compared to the boronic acid and thus, at suitable pH, binding of vicinal diols results in the formation of the charged boronate ester. Due to favourable stereochemistry, the binding constant is significantly greater when the boronic acid is in the tetrahedral form (Bosch et al., 2004). A set of coupled equilibria resulting from these interactions is shown in FIG. 1. The $pK_{a(1)}$ of phenylboronic acid has been reported to be around 8.9; thus, the tetrahedral boronate, which binds cis-diols much more readily than the trigonal form, is present at very low concentrations at physiological pH. Development of boronic acid ligands for physiological glucose detection has focused on reducing the $pK_a$ via synthetic modification of the boronic acid receptor (Wiskur et al., 2001). It is known that a charge stabilisation mechanism helps stabilize the formation of the boronate-vicinal diol diester (Badugu et al, 2005).

Optical measurements offer particular advantages for non-invasive glucose monitoring because they circumvent the practical difficulties associated with electrical connections to the sensor device. However, both chromophore and fluorophore-functionalised receptors are susceptible to photochemical instability. In addition, fluorescence measurements in biological media can be complicated by background fluorescence, low fluorophore solubility and oxygen interference.

Polymeric sensors can be fabricated that are optically responsive to receptor-ligand binding via changes to their diffraction properties. Glucose-responsive have been reported, based on phenylboronic acid-functionalised polymers (Alexeev et al., 2003). However, the fabrication of these materials is time-consuming and may not be suitable for mass manufacture.

WO95/26499 discloses a holographic sensor, based on a volume hologram. The sensor comprises a holographic element, the element comprising an analyte-sensitive holographic support medium having an optical transducing structure disposed throughout its volume. Because of this physical arrangement of the transducer, the optical signal generated by the sensor is very sensitive to volume changes or structural rearrangements taking place in the analyte-sensitive matrix as a result of interaction or reaction with the analyte. For example, a sensor comprising a gelatin-based holographic medium may be used to detect trypsin. Trypsin acts on the gelatin medium, irreversibly destroying the integrity of the holographic support medium.

WO03/087899 describes a method for the continuous detection of an analyte in a fluid involving the use of a holographic sensor. The support medium of the sensor comprises a group which is capable of reacting reversibly with the analyte. Thus, when fluid is passed over the holographic element, any analyte present can be detected continuously.

In particular, WO03/087899 describes how a holographic sensor formed by the polymerisation of monomers including vinyiphenylboronic acid may be used to detect glucose. The pendant phenylboronic acid groups can react reversibly with a vicinal diol group of glucose, resulting in swelling of the holographic support medium.

WO04/081624 is based on the discovery of a class of phenylboronic acid derivatives which allow for the detection of glucose and other vicinal diol-containing analytes across a wide range of pH values. These phenylboronic acids can be modified to promote formation of a more reactive tetrahedral conformation at low pH values.

For example, the phenyl group may comprise one or more electron-withdrawing substituents which, by mediating their electronic effects through the phenyl ring, promote formation of $RB(OH)_3^-$. As another example, a substituent may be capable of forming an intramolecular bond with the boron atom, forcing the boronate into a substantially tetrahedral conformation. Judicious selection of substituents allows the responsiveness of the sensor to be optimised with respect to a particular set of detection conditions.

WO04/081624 discloses a sensor for the detection of an analyte comprising a vicinal diol moiety, which comprises a holographic element comprising a medium and a hologram disposed throughout the volume of the medium, wherein an optical characteristic of the element changes as a result of a variation of a physical property occurring throughout the volume of the medium, and wherein the medium comprises a polymer comprising a group of formula (i)

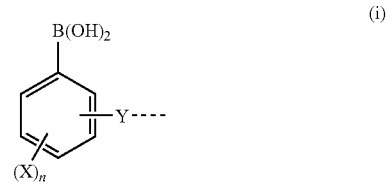

wherein
n is 0, 1, 2, 3 or 4;
each X (if present) is independently an atom or group which, via an electronic effect, promotes formation of a tetrahedral geometry about the boron atom; and Y is a spacer which, when n is 0 or otherwise optionally, is an atom or group which, via an electronic effect, promotes formation of a tetrahedral geometry about the boron atom.

Such a sensor can be used in a method for the detection of an analyte comprising a vicinal diol moiety in a fluid, which comprises contacting the fluid with the holographic element and detecting any change of the optical characteristic of the element. The analyte may comprise a plurality of vicinal diol moieties; examples of such analytes include glucose and tartaric acid.

WO04/081624 also discloses that in addition to a compound of formula (i), the monomers may include (meth) acrylamide and/or (meth)acrylate-derived co-monomers. In particular, the monomer HEMA (hydroxyethyl methacrylate) is readily polymerisable and cross-linkable. PolyHEMA is a versatile support material since it is swellable, hydrophilic and widely biocompatible. The monomers may also include co-monomers having groups which are capable of intermolecular electron-donation, for example secondary or tertiary amines.

Glucose-responsive holographic sensors, functionalised with 4-vinylphenylboronic acid (4-VBPA), based on acrylamide co-polymer hydrogel films are described elsewhere in more detail (Kabilan et al., 2004a). Upon glucose binding, the conversion of the electron-deficient $sp^2$-hydridised boron to the charged boronate causes a reversible swelling of the hydrogel matrix and a red-shift of the diffraction maxima. Whilst validating the concept of utilising holographic sensors as reporters of glucose concentration, the sensors operated at non-physiological pH values. Subsequent optimisation of the boronic acid moiety enabled the construction of a holographic glucose sensor that responds under physiological pH conditions (Kabilan et al., 2005). Furthermore, in these studies, it was found that the selectivity of the glucose-responsive holographic sensors for glucose in preference to lactate could be tuned by controlling the receptor concentration. Further modification of the polymeric microenvironment with tertiary amine groups has also been shown to improve the selectivity of the sensor for glucose over lactate (Kabilan et al., 2004b).

SUMMARY OF THE INVENTION

It has now been discovered that a cationic species such as a quaternary amine is particularly useful in the context of the above discussion. In particular, such species may allow greater selectivity for glucose.

It will be apparent from the description that a quaternary amine-modified glucose-responsive hydrogel matrix may be used to fabricate holographic sensors with enhanced selectivity for glucose. The addition of a charged quaternary ammonium group to the polymer structure caused a dramatic change to the glucose response characteristics, resulting in the observation of a blue-shift in the diffraction peak wavelength and an increase in the selectivity of the sensor for glucose compared with other sugars and the α-hydroxy acid, lactate. The observed response to glucose is based on bivalent binding of glucose by two phenylboronate receptors. At physiological fructose concentrations, there was no significant perturbation to glucose detection. The hydrogel films described herein and their glucose selective contraction may also be of use in fluorescence detection methods involving a dye and quencher or a FRET-based system involving a donor and acceptor.

According to a first aspect of the present invention, a sensor comprises respective acceptor and donor compounds immobilised in or on a matrix including a glucose-binding boronate and a cationic species, whereby the spacing between the acceptor and donor compounds is reduced in the presence of glucose.

According to another aspect of the present invention, a holographic sensor comprises a glucose-binding boronate and a cationic species held on or within the sensor.

A further aspect of the present invention is a complex of a glucose-binding boronate and a quaternary ammonium compound.

DESCRIPTION OF PREFERRED EMBODIMENTS

Figure 1:
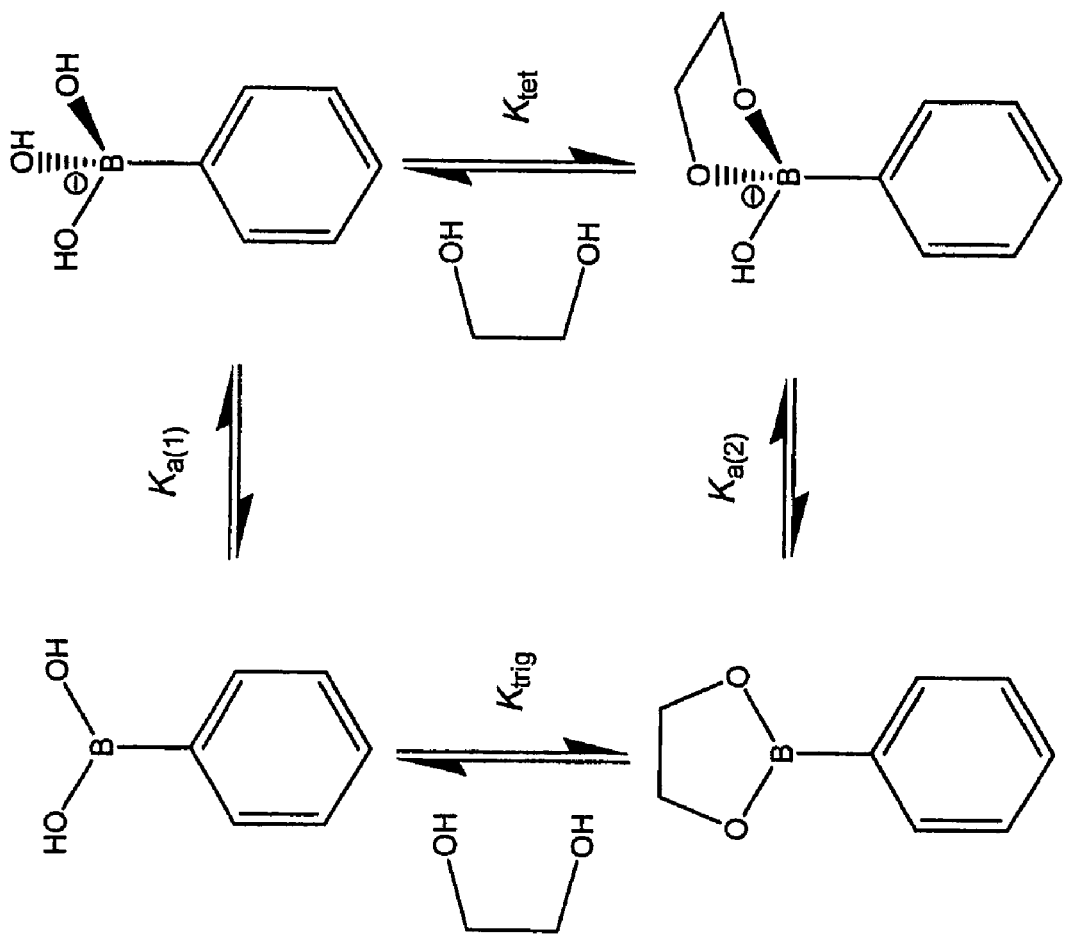
FIG. 1 shows the equilibria associated with phenylboronic acids in aqueous media, and the trigonal planar and charged tetrahedral forms.
Figure 2:
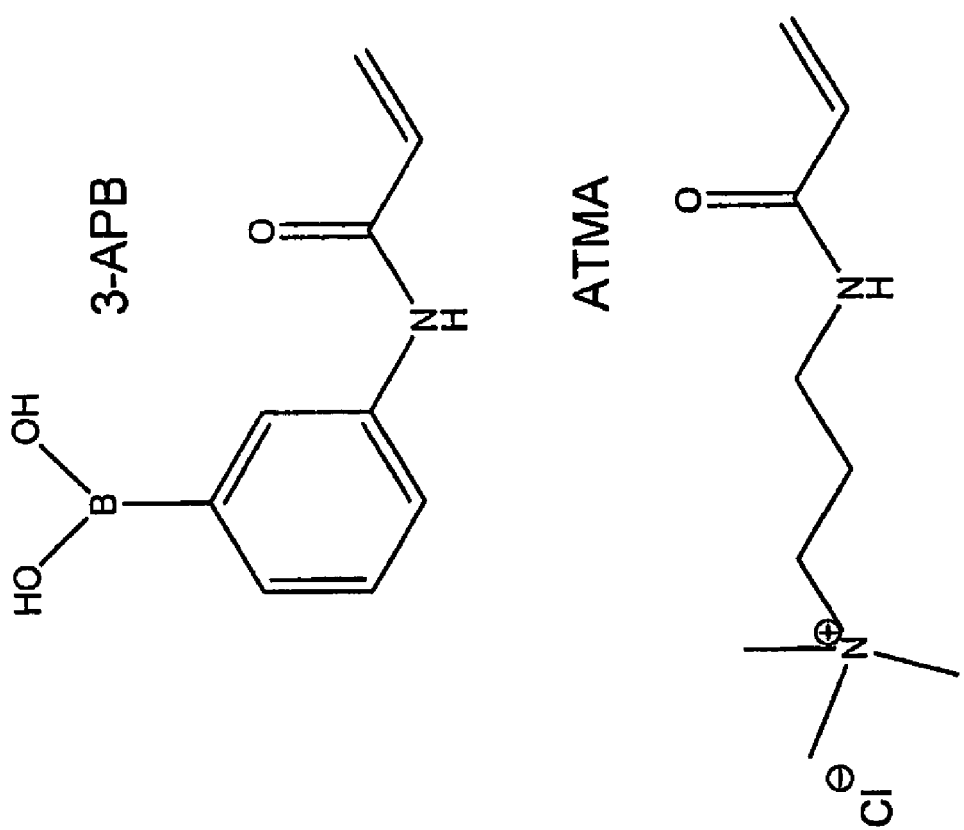
FIG. 2 shows the structures of a quaternary monomer, i.e. (3-acrylamidopropyl)trimethylammonium chloride (ATMA), and a phenylboronic acid receptor, i.e. 3-acrylamidophenylboronic acid (3-APB).

The invention is applicable to a variety of forms of sensor, and for qualitative or quantitative determination of glucose. The sensor may be in any suitable form, e.g. a contact lens or other optical implant. Thus, the invention may be embodied by, for example, a quartz crystal microbalance-based sensor, a surface plasmon resonance-based sensor, a total internal reflection-based sensor or, preferably (and described below for illustration), a holographic sensor.

The hologram itself may be made from materials known to those skilled in the art. Similarly, boronic acids are known. Reference may be made to the various documents referred to herein, including the WO publications.

The cationic species that may be used should be capable of immobilisation within the polymer or other medium. Phosphonium ions and preferably, quaternary amines are suitable for this purpose.

There are various embodiments of the invention. One is a contact lens (see WO2005/031442). Others are in detection systems using fluorescence/FRET, with a donor/acceptor pair or a quencher.

The fringe structure of the hologram may be made from a liquid crystal or the resulting diffraction pattern or image may be due to fringes produced by a liquid crystal. It will be understood that multiple liquid crystal types and multiple liquid crystal layers may be used.

Where a quaternary amine is used in a hologram, the hologram in the sensor can be generated by the diffraction of light. The hologram may only be visible under magnification, or may be viewable under white light, UV light or infra-red radiation or under specific temperature, magnetism or pressure conditions. The holographic image is preferably of an object or gives a 2- or 3-dimensional effect.

The sensor may further comprise means for producing an interference effect when illuminated with laser light. Preferably, such means comprises a depolarising layer.

The invention also relates to a method of detection of an analyte in a sample, which comprises contacting the sample with the medium of a sensor according to the invention, and detecting any change of the optical characteristic. The analyte is preferably glucose, and it may be detected in a sample of bodily fluid, e.g. blood or tears.

The change in optical characteristics can be detected by the naked eye or by using a device. The device is preferably selected from the group consisting of an optical reader, a mobile phone, a computer and a digital camera. It is envisaged that any type of computer can be used, such as a laptop, a desktop, or a hand held device such as a personal digital assistant (PDA) which is a personal organizer device.

The change in optical properties caused by interaction of the sensor with an analyte (known as the response) should be an obvious and non-ambiguous change in the colour or image of the hologram, preferably in the visible region of the electromagnetic spectrum. This gives an accurate and reliable readout that can be observed by the naked eye. To help ensure that this is achieved, the sensor preferably has an optical filter thereon. The optical filter should cover some or all of the surface (or surfaces) of the sensor which are observed to monitor analyte interaction.

The filter can be a lowpass filter (which allows radiation below a certain wavelength to pass through it), a highpass filter (which allows radiation above a certain wavelength to pass through it), or a bandpass filter (which allows radiation having a wavelength within a certain band, or certain bands in the case of a multi-bandpass filter, to pass through it). Hence, the use of such filters controls the frequency of the light that reaches the sensor. The hologram in the sensor acts like a bandpass reflector so the reflection wavelength of the hologram must be in the region of the filtered light to be transmitted back from the sensor to the observer or detector.

Filters are selected to provide a cut-off point for light of a high or low wavelength or both so can ensure that any response is in a particular range, for example, the visible range. They can be used to distinguish between different responses (for example to different analytes or analyte concentrations) which occur at different wavelength. They can also be used to prevent an ambiguous response if the sensor is used in non-optimal light conditions (for example, with monochromatic light). Optical filters can be specifically engineered to optimise the observed response to a specific analyte.

A transparent substrate is usually used in combination with an optical filter and is positioned between the sensor and the filter. Specular reflections from the filter and the transparent substrate are not observed.

An article comprising a sensor according to the invention can be used in various fields. Such an article may be a transaction card, banknote, passport, identification card, smart card, driving license, share certificate, bond, cheque, cheque card, tax banderole, gift voucher, postage stamp, rail or air ticket, telephone card, lottery card, event ticket, credit or debit card, business card, or an item used in consumer, brand or product protection for the purpose of distinguishing genuine products from counterfeit products or identifying stolen products.

Alternatively, the article may be an item of intelligent packaging. "Intelligent packaging" refers to a system that comprises part of, or an attachment to, a container, wrapper or enclosure, to monitor, indicate or test product information or quality or environmental conditions that will affect product quality, shelf life or safety and typical applications, such as indicators showing time-temperature, freshness, moisture, alcohol, gas, physical damage and the like.

The invention can be used with an article which is an industrial or handicraft item comprising a decorative element, selected from items of jewelry, items of clothing (including footwear), fabric, furniture, toys, gifts, household items (including crockery and glassware), architecture (including glass, tile, paint, metals, bricks, ceramics, wood, plastics and other internal and external installations), art (including pictures, sculpture, pottery and light installations), stationery (including greetings cards, letterheads and promotional material) and sporting goods, or an article which is a product or device for use in agricultural studies, environmental studies, human or veterinary prognostics, theranostics, diagnostics, therapy, chemical analysis or petrochemical analysis, especially which is a test strip, chip, cartridge, swab, tube, pipette, contact lens, sub-conjuctival implant, sub-dermal implant, breathalyser, catheter or a fluid sampling or analysis device. The sensor of the invention can be included on a transferable holographic film. The film is preferably present on a hot stamping tape. The security of an article can be enhanced by transferring onto the article the sensor from the film.

The invention also relates to a product comprising a sensor of the invention which is capable of generating data from said sensor and to a system which uses data generated by such a product.

The following Examples illustrate the invention.

Synthesis of Polymer Films

The appropriate quantity of each monomer was dissolved to give a monomer solution with the required molar ratios. The monomers were dissolved in 2% DMPA (w/v) in DMSO at a ratio 1:2.21 (w/v) of monomers to solvent. A 100 µL aliquot of monomer solution was layered onto the polyester surface of an aluminised polyester sheet. A glass microscope slide, pre-treated with 3-(trimethoxysilyl)propyl methacrylate [Mayes et al., 1999], was then lowered, silane-treated side down, onto the monomer mixture. Films were polymerised by a UV-initiated free radical reaction at 20° C. for 60 min. Polymerised films were peeled off the polyester sheet whilst submerged in deionised water, and the edges of each film were cleaned with a scalpel blade to remove any excess material prior to hologram construction.

Hologram Construction

Holograms were constructed using a diffusion method as described previously (Blyth et al., 1999). The polymer films were placed face-down onto 400 µl of 0.3 M aqueous silver nitrate solution for 2 min. Excess solution was wiped off and the film was dried in a stream of warm air. Under red-safe lighting, the slides were placed film side up in 40 mL of 4% (w/v) KBr and 0.05% (w/v) ascorbic acid in 1:1 methanol/$H_2O$ (v/v) with 1 mL of 0.1% (w/v) QBS dye in methanol and agitated for 1 min. The films were rinsed with distilled water and immersed polymer side down into the hologram exposure bath containing PBS, pH 7.4, for 10 min. The whole area of the slide was then exposed to three pulses from a frequency-doubled (532 nm) Nd:YAG laser. The slide was removed from the exposure bath and agitated for ~10 s in freshly made modified Saxby developer solution (40 mL of 20 g/L ascorbic acid, 3 g/L 4-methylaminophenol sulfate, 50 g/L sodium carbonate, 15 g/L sodium hydroxide) (Saxby, 1994). The developed hologram was rinsed under distilled water and immersed in stop solution (5% (v/v) aqueous acetic acid). After rinsing under distilled water, the film was immersed for 5 min in agitated 20% (w/v) aqueous sodium thiosulfate to remove any undeveloped silver and rinsed in methanol and then distilled water.

Monitoring Holographic Responses

Single strips of hologram, ~8 mm wide, were cut from a slide and inserted into a 4 mL plastic cuvette with the film side facing inward. PBS (1 mL) was added and the cuvette left to equilibrate at 30° C. in a temperature-controlled cuvette holder. An Avantes AVS-MC2000-2 reflection spectrophotometer equipped with AvaSoft 5 processing software was used to measure the wavelength of light reflected from a white light source by the hologram as determined by spacing of the fringes within the polymer. The response of the sensor to the addition of aliquots of 0.1 M sugar in PBS was recorded after equilibration of the sugar solutions overnight to ensure that the relative proportion of isomers present would mimic the equilibrium mixture found in media or biological fluids. Between each addition, the sensor was allowed to equilibrate to a stable diffraction wavelength. A 2×5 mm magnetic follower (Fisher) and stirrer arrangement was used to ensure constant agitation.

Fabrication of Glucose-Responsive Holograms

Stable hydrogel films (~10 μm thick) were fabricated by copolymerising acrylamide with 3 or 5 mol % N,N'-methylenebisacrylamide cross-linker (MBA), 4 or 12 mol % ATMA and 12 mol % 3-APB. Photosensitive films were formed by diffusing in silver nitrate and then potassium bromide containing a dye, QBS, to generate a polymer matrix containing ultra-fine grains (<20 nm diameter) of AgBr. Subsequent illumination with laser light in PBS buffer solution (pH 7.4, I~150 mM) followed by a development step generated an interference pattern of silver fringes spaced λ/2 apart within the thickness of the polymer film. The monochromatic image of the plane mirror resulted in the observation of a characteristic spectral peak with a wavelength described by the Bragg equation.

Effect of Saccharide

Figure 3:
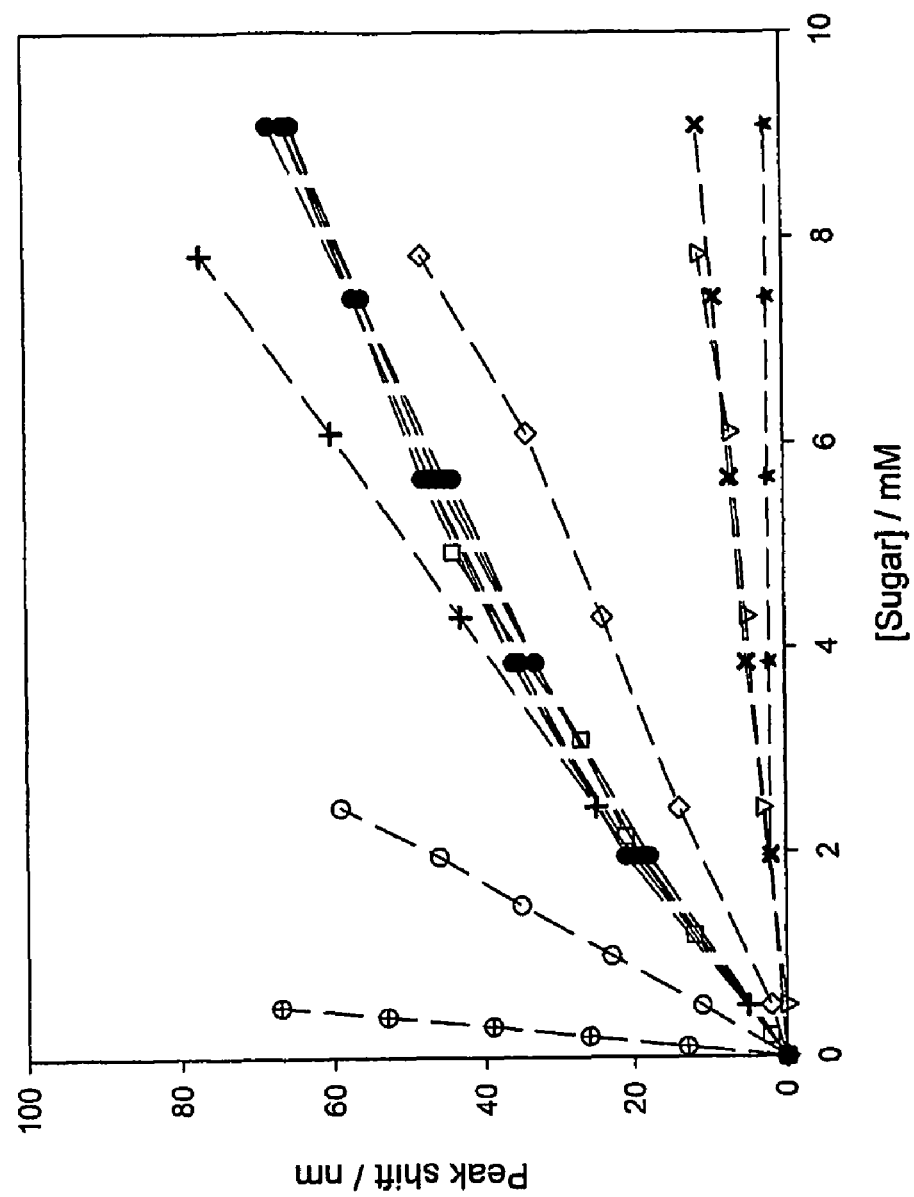
FIG. 3 is a graph showing the shift in the diffraction wavelength of a 3 mol % MBA, 12 mol % 3-APB hologram in response to the sugars: Fructose (⊕), Xylose (●), Galactose (+), Maltose (×), Ribose (○), Mannose (⊘), Lactose (♦), Sucrose (↑), and Glucose (●). The response of the sensor to glucose was measured before each sugar to check reproducibility (for glucose N=8, for the other sugars N=1).

The response of acrylamide holograms prepared with 3 mol % MBA and 12 mol % 3-APB was examined in the presence of 0-9 mM of various sugars. The results are shown in FIG. 3. A red-shift in the position of the diffraction peak wavelength, due to the volumetric expansion of the hydrogel, was observed in the presence of all sugars except sucrose. The expansion is most likely to be due to the formation of charged boronate groups, which generates a Donnan potential and causes the osmotic flow of water into the polymer. The mechanism for the response, according to the scheme shown in FIG. 1, is proposed to be the reduction of the boronic acid $pK_a$ caused by binding of vicinal diols, which then results in the formation of more charged boronate groups. The magnitude of the peak shift is correlated to the charge generated in the matrix by saccharide binding. Thus it is expected that the sensitivity of the sensor to different saccharides will be affected by differences in both the binding constant and the $pK_a$ shifts.

It was found that the diffraction peak shift was more sensitive to fructose, ribose and galactose than glucose. The sensitivity to xylose and mannose was similar to that for glucose, whereas the sensor was much less sensitive to the disaccharides lactose, maltose and sucrose. Like glycosylated proteins, these may not be able to enter the hydrogel because of their larger size, a factor contributing to the sensor's selectivity. A near-linear relationship between the sugar concentration and the peak shift was observed with all sugars tested. Comparison of the sensitivity of the holographic sensor to different sugars revealed that variability of the fructose concentration may, even at physiological levels (<0.1 mM), interfere with a reliable blood glucose measurement.

Figure 4:
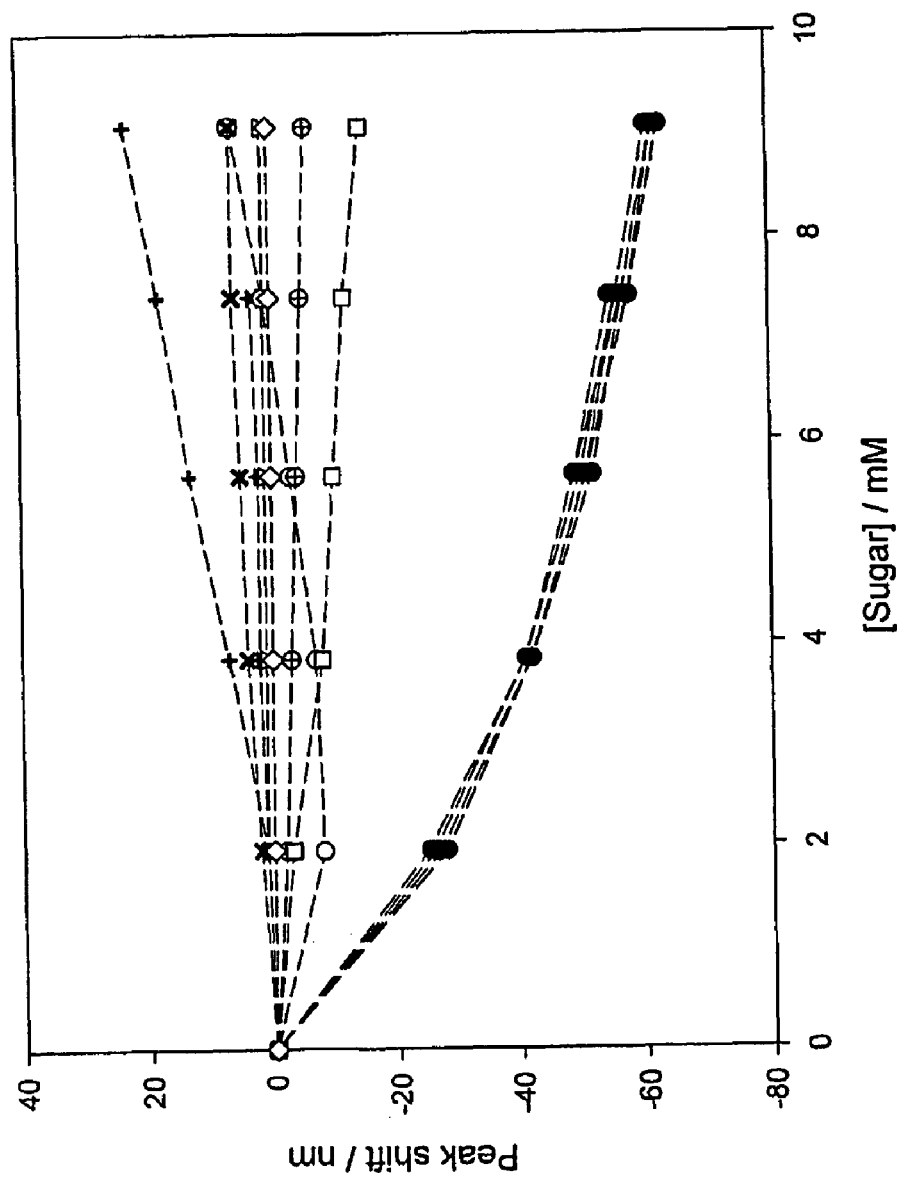
FIG. 4 is a graph showing the response of holograms containing 3 mol % MBA, 12 mol % 3-APB and 12 mol % ATMA to the sugars: Maltose (↑), Mannose (♦), Mannitol (○), Galactose (β), Ribose (×), Fructose (+), Xylose (●), Sucrose (⊘), and Glucose (●). The response of the sensor to glucose was measured before each sugar to check reproducibility (for glucose N=7, for the other sugars N=1).
Figure 5:
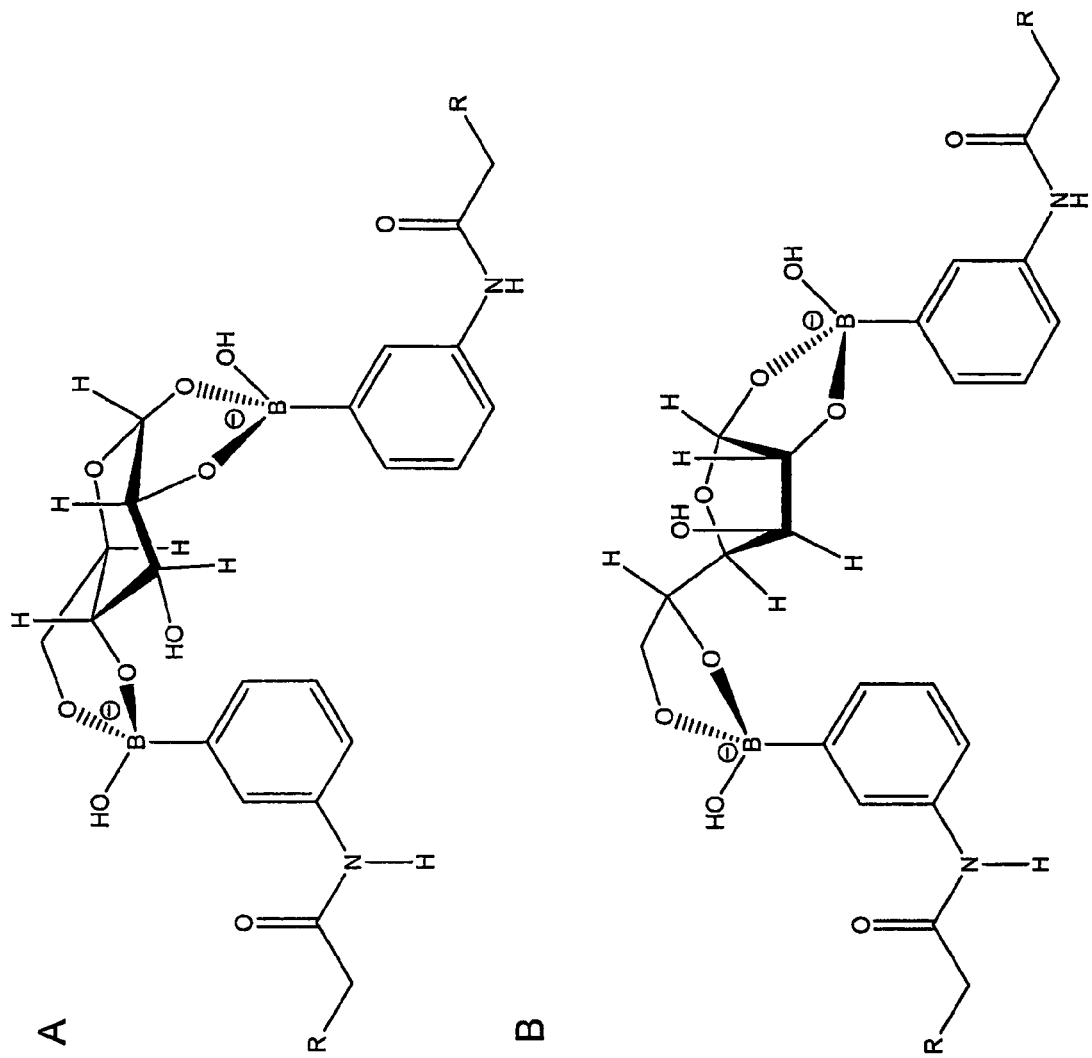
FIG. 5 shows two of the possible ways glucose may bind and cross-link two phenylboronic acid receptors, (a) through the 1,2 and 4,6 positions of the pyranose (chair) form of glucose and (b) through the 1,2 and 5,6 positions of the furanose form of glucose.

The optical response of films containing 3 mol % MBA, 12 mol % 3-APB and 12 mol % ATMA was tested in a similar range of sugar solution's. It was found that glucose caused a blue-shift in the peak wavelength of the holographic film (FIG. 4). This shift indicates that the response mechanism in operation is different to that observed in the films not containing ATMA. The origin of the blue-shift in the diffraction maxima, due to volumetric contraction of the film perpendicular to the fringe planes, is proposed to be the cross-linking of two boronic acid receptors with favourable stereochemistry by glucose to give a bis-boronate-glucose complex and an accompanying increase in the hydrogel elastic constant. The positively charged quaternary amines help stabilise the negatively charged boronate form of 3-APB through a 'charge-neutralisation stabilisation' mechanism (Badugu et al., 2005), wherein cross-linking by glucose is promoted. Possible binding modes are shown for the pyranose (chair) and furanose forms in FIG. 5.

The ATMA-modified films were found to be significantly less sensitive to all the other sugars tested. The response to added fructose was dramatically reduced compared to the unmodified film. The interferent sugars tested only caused a minimal volumetric change. The reduced swelling observed may also be due in part to cross-linking. However, for saccharides other than glucose, cross-linking is reported to be much less favourable (Alexeev et al., 2003). The lack of noticeable swelling is most likely due to a reduction in charge repulsion between positively charged ATMA groups upon receptor-ligand binding and the formation of the boronate diester. For fructose, a small red-shift is observed; this is most likely due to its higher affinity for phenylboronic acids and the predominant formation of boronate groups on binding leading to osmotic swelling.

Table 1 (shown below) shows the approximate sensitivities of 3 mol % MBA holograms to sugars. The figures correspond to the peak shift for a sugar concentration of 5.66 mM (near the mid-point of the normal physiological range for healthy adults i.e. 4-8 mM).

Comparison of the sensitivities of the 12 mol % ATMA-containing films with the control polymer, as shown in Table 1, demonstrates that the modification significantly reduces the sensitivity to potentially interfering sugars, particularly fructose. Based on this, variations in fructose or galactose levels at physiological concentrations (<0.1 mM) are unlikely to constitute significant interferents to a reliable glucose measurement using the ATMA-modified sensor.

TABLE 1

| Sugar | Peak shift for 5.66 mM sugar 12 mol % 3-APB | Peak shift for 5.66 mM sugar 12 mol % 3-APB + 12 mol % ATMA |
|---|---|---|
| Glucose | +40 nm | −50 nm |
| Fructose | +761 nm | +13 nm |
| Xylose | +50 nm | −10 nm |
| Galactose | +55 nm | −4 nm |
| Maltose | +7 nm | +2 nm |
| Ribose | +121 nm | +5 nm |
| Mannose | +34 nm | +1 nm |
| Lactose | +8 nm | ND |
| Sucrose | +1 nm | 0 nm |

Response of Glucose-Sensitive Holograms to Lactate and Fructose

The response of the sensor hologram to lactate, an α-hydroxy acid, was investigated, as lactate is a potential interferent for blood glucose measurements, being present in blood at concentrations of approximately 0.36-0.75 mM.

Figure 6:
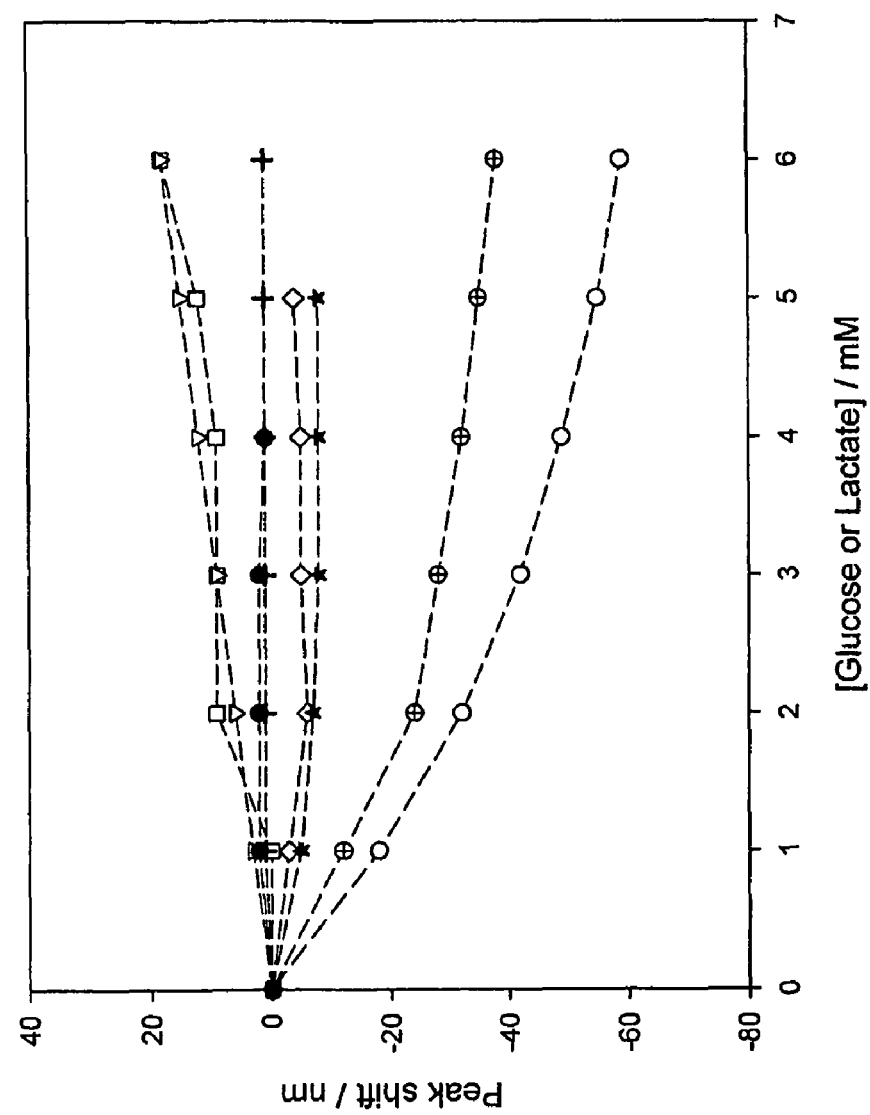
FIG. 6 is a graph showing the response to glucose and lactate of holograms containing 3 or 5 mol % MBA, 12 mol % 3-APB and 4 or 12 mol % ATMA. Glucose+5 mol % MBA, 12 mol % 3-APB, 4 mol % ATMA (⊘), Lactate+5 mol % MBA, 12 mol % 3-APB, 4 mol % ATMA (●), Glucose +5 mol % MBA, 12 mol % 3-APB, 12 mol % ATMA (⊕), Lactate+5 mol % MBA, 12 mol % 3-APB, 12 mol % ATMA (+), Glucose+3 mol % MBA, 12 mol % 3-APB, 4 mol % ATMA (↑), Lactate+3 mol % MBA, 12 mol % 3-APB, 4 mol % ATMA (♦), Glucose+3 mol % MBA, 12 mol % 3-APB, 12 mol % ATMA (○), Lactate+3 mol % MBA, 12 mol % 3-APB, 12 mol % ATMA (●).

Holograms composed of 12 mol % 3-APB and 4 or 12 mol % ATMA were tested in glucose or lactate solutions of 0 to 6 mM. The results are shown in (FIG. 6).

It was found that the lactate response was completely attenuated using 3 and 5 mol % MBA and 12 mol % ATMA. Both films responded to glucose, with a negative peak shift of approximately 10 nm mM$^{-1}$ or 5 nm mM$^{-1}$ for 3 and 5 mol % MBA, respectively. The greater response of the hologram containing 3 mol % MBA may be attributed to the hydrogel being more highly swollen initially, and therefore able to contract to a greater extent.

Figure 7:
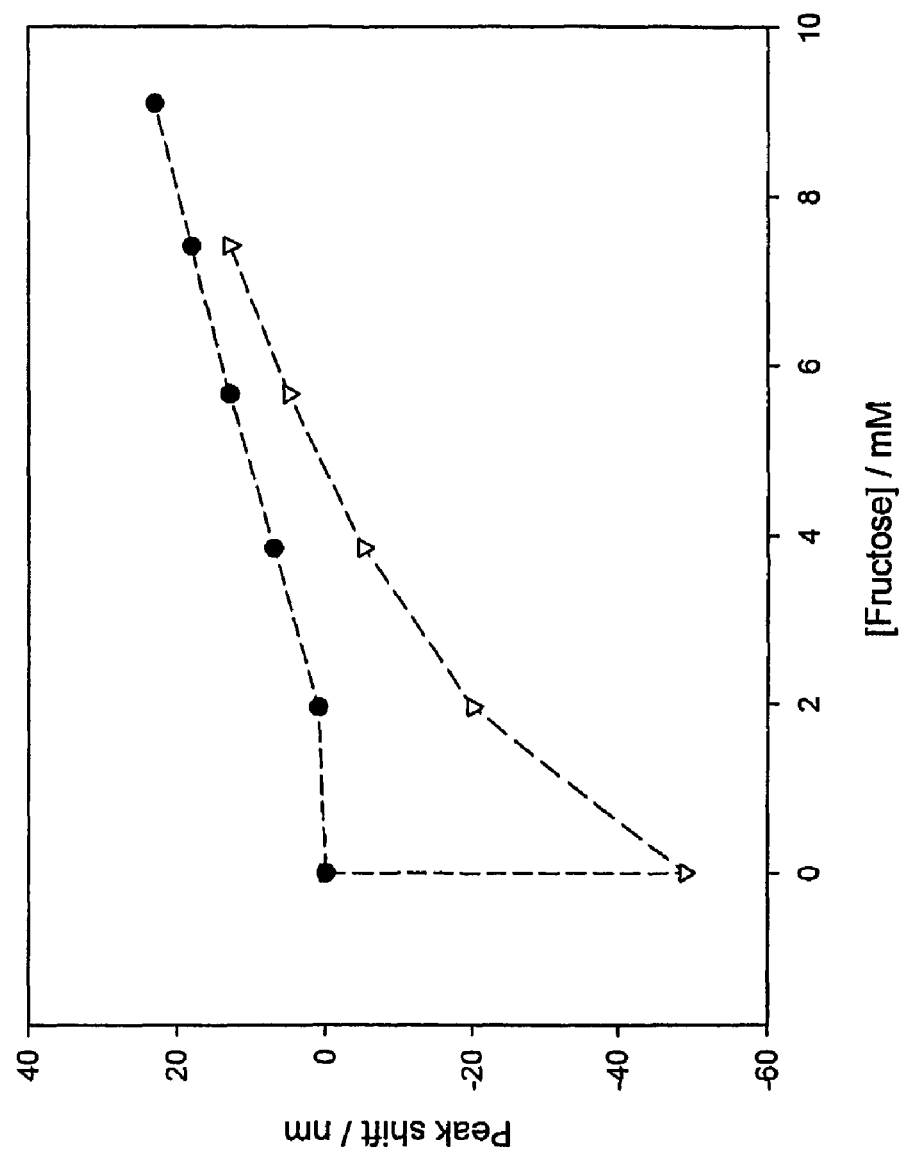
FIG. 7 is a graph showing fructose response.

As shown in FIG. 7, it was found that addition of 2 mM fructose, after 6 mM glucose had been added, caused the partial reversal of the negative peak shift. Further additions to 6 mM fructose fully reversed the negative peak shift. Interestingly, after the addition of approximately 8 mM fructose, the response of the hologram either with or without 6 mM added glucose was virtually identical. This indicates that the phenylboronic acid is preferentially binding fructose, thus breaking the cross-linked structure associated with divalent glucose binding. Furthermore, this supports the proposal that receptor cross-linking is responsible for the contractile response to glucose binding observed in the ATMA containing films. To further investigate the effect, the ATMA hologram was titrated with glucose up to 56 mM. Even at these high concentrations, there was no red-shift associated with saturation of the boronate-binding sites and a shift in the equilibrium from a bisboronate-glucose complex towards a 1:1 association between boronic acid and glucose. This is in contrast to results with colloidal crystalline arrays wherein response to glucose, the sensor initially showed a blue-shift due to contraction and then showed a red-shift corresponding to swelling, behaviour which would complicate the sensor's use in real applications (Alexeev et al., 2003).

The fructose concentration in blood is typically found at <0.1 mM, compared to glucose at 4-8 mM, and it is therefore unlikely to interfere with glucose measurements in physiological fluids. To confirm this, the 3 mol % MBA, 12 mol % 3-APB, 12 mol % ATMA sensor hologram was tested in the presence of a background of 0.1 mM fructose for its response to glucose across the range 2-6 mM. The percentage change in response to glucose due in the presence of 0.1 mM fructose was between 2% (6 mM glucose) and 7% (2 mM glucose) compared to control tests performed in the absence of fructose. The error in the measurement from repeated readings (N=3) was calculated to be approximately 5%, thus demonstrating the potential for these holographic sensors to selectively detect glucose concentration in complex biological media.

REFERENCES

Alexeev et al, 2003; Anal. Chem. 75, 2316-2323.
Badugu et al, 2005; Talanta 65 (3), 762-768.
Blyth et al, 1999; Imag. Sci. J. 47 (2), 87-91.
Bosch et al, 2004; Tetrahedron 60, 11175-11190.
Kabilan et al, 2004a; J. Mol. Recog. 17 (3), 162-166.
Kabilan et al, 2004b; Sensors, 2004. Proceedings of IEEE 2, 1003-1006.
Kabilan et al, 2005; Biosensors and Bioelectronics, 20, 1602-1610.
Mayes et al, 1999; Anal. Chem. 71, 3390-3396.
Saxby, 1994;. Practical Holography, 2nd ed. Prentice Hall, London.
Wiskur et al, 2001; Org. Lett. 3, 1311-1314.

All publications identified herein are incorporated herein by reference.

The invention claimed is:

1. A holographic sensor comprising a holographic element and a matrix, wherein the matrix comprises a glucose-binding boronate and a quaternary ammonium compound.

2. The sensor according to claim 1, further comprising means for producing an interference effect when illuminated with laser light.

3. The sensor according to claim 2, wherein the means comprises a depolarising layer.

4. The sensor according to claim 1, which has an optical filter thereon.

5. The sensor according to claim 4, wherein the optical filter is a bandpass filter.

6. An article comprising a sensor according to claim 1, which is a test strip, chip, cartridge, swab, tube, pipette, contact lens, sub-conjunctival implant, sub-dermal implant, breathalyser, catheter or a fluid sampling or analysis device.

7. A method of detection of an analyte in a sample, which comprises contacting the sample with the medium of a holographic sensor, and detecting any change of the optical characteristic wherein the sensor comprises respective acceptor and donor compounds immobilised in or on a matrix including a glucose-binding boronate and a quaternary ammonium or phosphonium compound.

8. An article comprising a sensor according to claim 1, which is a transaction card, banknote, passport, identification card, smart card, driving license, share certificate, bond, cheque, cheque card, tax banderole, gift voucher, postage stamp, rail or air ticket, telephone card, lottery card, event ticket, credit or debit card, business card, or an item used in consumer, brand or product protection for the purpose of distinguishing genuine products from counterfeit products or identifying stolen products.

9. The method according to claim 7, wherein the analyte is a chemical, biochemical, or biological species.

10. The sensor according to claim 1, wherein the quaternary ammonium compound comprises (3-acrylamidopropyl) trimethylammonium.

11. The sensor according to claim 1, wherein the glucose-binding boronate is 3-acrylamidophenylboronic acid.

12. The sensor according to claim 1, wherein at least one of the quaternary ammonium compound and the glucose-binding boronate is a monomer unit of the matrix.

13. A holographic sensor comprising a holographic element and a matrix, wherein the matrix comprises a glucose-binding boronate and a quaternary phosphonium compound.

14. The sensor according to claim 13, further comprising means for producing an interference effect when illuminated with laser light.

15. The sensor according to claim 14, wherein the means comprises a depolarising layer.

16. The sensor according to claim 13, which has an optical filter thereon.

17. An article comprising a sensor according to claim 13, which is a test strip, chip, cartridge, swab, tube, pipette, contact lens, sub-conjunctival implant, sub-dermal implant, breathalyser, catheter or a fluid sampling or analysis device.

18. An article comprising a sensor according to claim 13, which is a transaction card, banknote, passport, identification card, smart card, driving license, share certificate, bond, cheque, cheque card, tax banderole, gift voucher, postage stamp, rail or air ticket, telephone card, lottery card, event ticket, credit or debit card, business card, or an item used in consumer, brand or product protection for the purpose of distinguishing genuine products from counterfeit products or identifying stolen products.

19. The sensor according to claim 13, wherein the glucose-binding boronate is 3-acrylamidophenylboronic acid.

20. The sensor according to claim 13, wherein at least one of the quaternary phosphonium compound and the glucose-binding boronate is a monomer unit of the matrix.

21. The method according to claim 7, wherein the analyte comprises 2 cis-diol units.

22. The method according to claim 7, wherein the analyte is a monosaccharide or a disaccharide.

23. The method according to claim 7, wherein the analyte is glucose.

24. The method according to claim 7, wherein the change in optical characteristic is a shift in the color or image of the hologram.

25. The method according to claim 7, wherein the change in optical characteristic is a shift in the color of the hologram, and wherein the color of the hologram is in the visible range.

26. The method according to claim 25, wherein the shift in color is a reduction in the wavelength of an image of the hologram.

\* \* \* \* \*